(12) United States Patent
Cook

(10) Patent No.: US 9,557,304 B2
(45) Date of Patent: Jan. 31, 2017

(54) PRE-COLUMN HEATING OF MOBILE PHASE SOLVENT IN CHROMATOGRAPHY SYSTEMS

(71) Applicant: Waters Technologies Corporation, Milford, MA (US)

(72) Inventor: Michael J. Cook, Franklin, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 143 days.

(21) Appl. No.: 14/381,383

(22) PCT Filed: Feb. 12, 2013

(86) PCT No.: PCT/US2013/025661
§ 371 (c)(1),
(2) Date: Aug. 27, 2014

(87) PCT Pub. No.: WO2013/133934
PCT Pub. Date: Sep. 12, 2013

(65) Prior Publication Data
US 2015/0135861 A1 May 21, 2015

Related U.S. Application Data

(60) Provisional application No. 61/608,133, filed on Mar. 8, 2012.

(51) Int. Cl.
*G01N 30/30* (2006.01)
*G01N 30/06* (2006.01)

(52) U.S. Cl.
CPC .............. *G01N 30/06* (2013.01); *G01N 30/30* (2013.01); *G01N 2030/3046* (2013.01); *G01N 2030/3061* (2013.01)

(58) Field of Classification Search
CPC ........ G01G 30/00; G01N 30/02; G01N 30/04; G01N 30/06; G01N 30/30; G01N 2030/3036; G01N 2030/3061
See application file for complete search history.

(56) References Cited

U.S. PATENT DOCUMENTS 3,213,596 A * 10/1965 Gill .................. G01N 30/30
 73/23.25
3,522,725 A * 8/1970 Waters ............... G01N 21/4133
 210/198.2

(Continued)

FOREIGN PATENT DOCUMENTS

DE 3541641 5/1987
DE 20304609 6/2003

(Continued)

OTHER PUBLICATIONS

International Search Report for International Application No. PCT/US2013/025661 dated Apr. 16, 2013, 3 pages.

(Continued)

*Primary Examiner* — Nguyen Ha
(74) *Attorney, Agent, or Firm* — Schmeiser, Olsen & Watts LLP

(57) ABSTRACT

An apparatus for heating a flowing fluid includes a tubing assembly, a heater block made of thermally conductive material, and a heater cartridge in thermal communication with the heater block. The heater cartridge is configured to provide heat to the heater block for transfer to fluid flowing through the tubing assembly. The apparatus also includes circuitry in electrical communication with the heater cartridge to control a temperature of the heater block by controlling operation of the heater cartridge. The heater block is die-cast about the tubing assembly.

18 Claims, 19 Drawing Sheets

(56) References Cited

U.S. PATENT DOCUMENTS

| | | | |
|---|---|---|---|
| 4,026,803 | A | 5/1977 | Abrahams et al. |
| 4,350,586 | A | 9/1982 | Conlon et al. |
| 5,032,283 | A | 7/1991 | Scott et al. |
| 5,393,239 | A | 2/1995 | Ursich |
| 5,601,707 | A | 2/1997 | Clay et al. |
| 5,983,710 | A | 11/1999 | Uhen et al. |
| 6,197,198 | B1 | 3/2001 | Messinger et al. |
| 6,442,341 | B1 | 8/2002 | Wu |
| 7,258,726 | B2 | 8/2007 | Ledford, Jr. |
| 7,326,893 | B2 | 2/2008 | Kanzaki et al. |
| 7,731,463 | B2 | 6/2010 | Davis et al. |
| 8,613,216 | B2 | 12/2013 | Vorm |
| 2003/0061867 | A1 | 4/2003 | Gerner |
| 2006/0054558 | A1 | 3/2006 | Jones et al. |
| 2008/0277345 | A1 | 11/2008 | Prentice et al. |
| 2013/0052083 | A1* | 2/2013 | Kirby ............... F24H 1/142 422/70 |
| 2013/0277350 | A1 | 10/2013 | Arima |
| 2015/0135861 | A1 | 5/2015 | Cook |

FOREIGN PATENT DOCUMENTS

| | | |
|---|---|---|
| WO | 2010138678 A1 | 12/2010 |
| WO | 2011085359 A1 | 7/2011 |

OTHER PUBLICATIONS

International Written Opinion for International Application No. PCT/US2013/025661 dated Apr. 16, 2013, 5 pages.

Extended European Search Report in related European Patent Application No. 11732307.1, mailed on May 30, 2016; 13 pages.

International Preliminary Report on Patentability in related International Patent Application No. PCT/US11/20803, mailed on Jul. 26, 2012; 8 pages.

Partial Search Report in related European Patent Application No. 11732307.1, mailed on Feb. 3, 2016; 8 pages.

International Preliminary Report on Patentability in counterpart International Patent Application No. PCT/US13/25661, mailed on Sep. 18, 2014; 7 pages.

International Search Report & Written Opinion in related International Patent Application No. PCT/US11/20803, mailed on Mar. 29, 2011; 8 pages.

Notice of Allowance in related U.S. Appl. No. 13/519,818, mailed on Apr. 22, 2016; 7 pages.

Non-Final Office Action in related U.S. Appl. No. 13/519,818, mailed on Jul. 7, 2015; 9 pages.

Final Office Action in related U.S. Appl. No. 13/519,818, mailed on Feb. 16, 2016; 11 pages.

Non-Final Office Action in related U.S. Appl. No. 15/249,720, mailed on Sep. 28, 2016; 9 pages.

* cited by examiner

PRE-COLUMN HEATING OF MOBILE PHASE SOLVENT IN CHROMATOGRAPHY SYSTEMS

RELATED APPLICATIONS

This application is the National Stage of International Application No. PCT/US2013/025661, filed on Feb. 12, 2013, which claims priority to and benefit of U.S. Provisional Patent Application No. 61/608,133 entitled "Pre-Column Heating of Mobile Phase Solvent in Chromatography Systems," filed Mar. 8, 2012. The contents and teachings of each of these applications are hereby expressly incorporated herein by reference in their entirety.

TECHNICAL FIELD

This disclosure relates generally to chromatography systems. More specifically, the disclosure relates to pre-column heating of mobile phase solvent in chromatography systems.

BACKGROUND

Chromatography is a set of techniques for separating a mixture into its constituents. Generally, in a liquid chromatography analysis, a pump system takes in and delivers a mixture of liquid solvents (and/or other fluids) to a sample manager, where a sample awaits injection into the solvents. The sample is the material under analysis. Examples of samples include complex mixtures of proteins, protein precursors, protein fragments, reaction products, and other compounds, to list but a few. In an isocratic chromatography application, the composition of the liquid solvents remains unchanged, whereas in a gradient chromatography application, the solvent composition varies over time. The mobile phase, comprised of a sample dissolved in a mixture of solvents (and/or other fluids), moves to a point of use, such as a column, referred to as the stationary phase.

By passing the mobile phase through the column, the various components in the sample separate from each other at different rates and thus elute from the column at different times. A detector receives the separated components from the column and produces an output from which the identity and quantity of the analytes may be determined. Temperature can influence the results of the analysis, affecting such properties as the separation performance of the column and the viscosity of a mobile phase. Therefore, maintaining an accurate constant column temperature is important to the accuracy and reproducibility of the results.

SUMMARY

An active pre-heater assembly is an electromechanical assembly used to condition mobile phase solvent to a specified temperature before it enters a chromatography column. Heat transfer takes place between a thermally conductive heater block containing a heater cartridge and a solvent tubing assembly which the mobile phase solvent travels through. This disclosure is based, in part, on the realization that die-casting a heater block about a solvent tubing assembly in an insert cast process can provide for improved manufacturability, reduced lead times, and/or reduced design costs associate with the assemblage of the heater block and the tubing assembly.

One aspect provides an apparatus for heating a flowing fluid. The apparatus includes a tubing assembly, a heater block made of thermally conductive material, and a heater cartridge in thermal communication with the heater block. The heater cartridge is configured to provide heat to the heater block for transfer to fluid flowing through the tubing assembly. The apparatus also includes circuitry in electrical communication with the heater cartridge to control a temperature of the heater block by controlling operation of the heater cartridge. The heater block is die-cast about the tubing assembly.

Another aspect features a thermal module for pre-heating liquid flowing into a liquid chromatography column. The thermal module includes a column compartment configured to hold a liquid chromatography column. The column compartment has an elongated trough compartment with two ends. One of the two ends having an electrical socket. The thermal module also includes a pre-heater assembly that is configured to plug into the electrical socket at the one end of the trough compartment. The pre-heater assembly includes a tubing assembly, a heater block made of thermally conductive material, and a heater cartridge in thermal communication with the heater block. The heater cartridge is configured to provide heat to the heater block for transfer to fluid flowing through the tubing assembly. The pre-heater assembly also includes circuitry in electrical communication with the heater cartridge to control a temperature of the heater block by controlling operation of the heater cartridge. The heater block is die-cast about the tubing assembly such that the restraining component inhibits the tubing from rotating within the heater block.

Implementations may include one or more of the following features.

In some implementations the thermal module also includes a second electrical socket disposed at the other end of the trough compartment and a trough slidable within the trough compartment. The trough is configured to hold a liquid chromatography column and to cover an unused one of the two electrical sockets.

In certain implementations, one end of the trough compartment has a groove for receiving the tubing.

In some implementations, the pre-heater assembly can also include a leaf-spring carrier having a pair of opposing springy prongs. The heater block assembly can be disposed between the prongs.

In certain implementations, the thermal module also includes a receptacle configured to snap into the electrical socket of the trough compartment and to receive the leaf-spring carrier.

In some implementations, the thermal module also includes a temperature sensor in thermal communication with the heater block to provide an indication of the temperature of the heater block. The circuitry is in electrical communication with the temperature sensor to determine therefrom the temperature of the heater block.

In certain implementations, the tubing assembly includes tubing, a tube sleeve welded around the tubing, and a restraining component welded around the tubing. The heater block can be die-cast about the tubing assembly such that the restraining component inhibits the tubing from rotating within the heater block.

In some implementations, the tubing includes a serpentine loop, and the heater block can be die-cast about the serpentine loop.

In certain implementations, the thermal module can also include a column fitting that is configured to couple an end of the tube sleeve that emerges from the heater block to an inlet port of a chromatography column.

In some implementations, the thermal module can also include a tube fitting that is configured to couple an end of the tubing extending outwardly from the heater block to an outlet port of a sample manager.

In certain implementations, the restraining component is a hexagonally shaped sleeve.

In some implementations, the thermal module can also include a strain relief component disposed about the tubing, and the heater block can be die-cast about a first end portion of the strain relief component.

In certain implementations, a second end portion of the strain relief component extends outwardly from the heater block.

In some implementations, the strain relief component comprises polymeric tubing.

Implementations can provide one or more of the following advantages.

Die-casting a heater block about a solvent tubing assembly in an insert cast process can provide for improved manufacturability, reduced lead times, and/or reduced design costs associate with the assemblage of the heater block and the tubing assembly.

The insert cast process can also allow for the addition of a strain relief component to the solvent tubing assembly, which can help to improve fatigue life of the solvent tubing assembly.

Die-casting a heater block about a solvent tubing assembly in an insert cast process can also better accommodate tubing with tortuous serpentine loops, as compared to conventional methods that include soldering tubing into a metal block. It is believed that the inclusion tortuous loops may be beneficial for reducing thermal insulative effects of fluidic boundary layers when working with supercritical fluids, such as in supercritical fluid chromatography systems.

Other aspects, features, and advantages are in the description, drawings, and claims.

BRIEF DESCRIPTION OF THE DRAWINGS

Like reference numbers indicate like elements.

DETAILED DESCRIPTION

Figure 1:
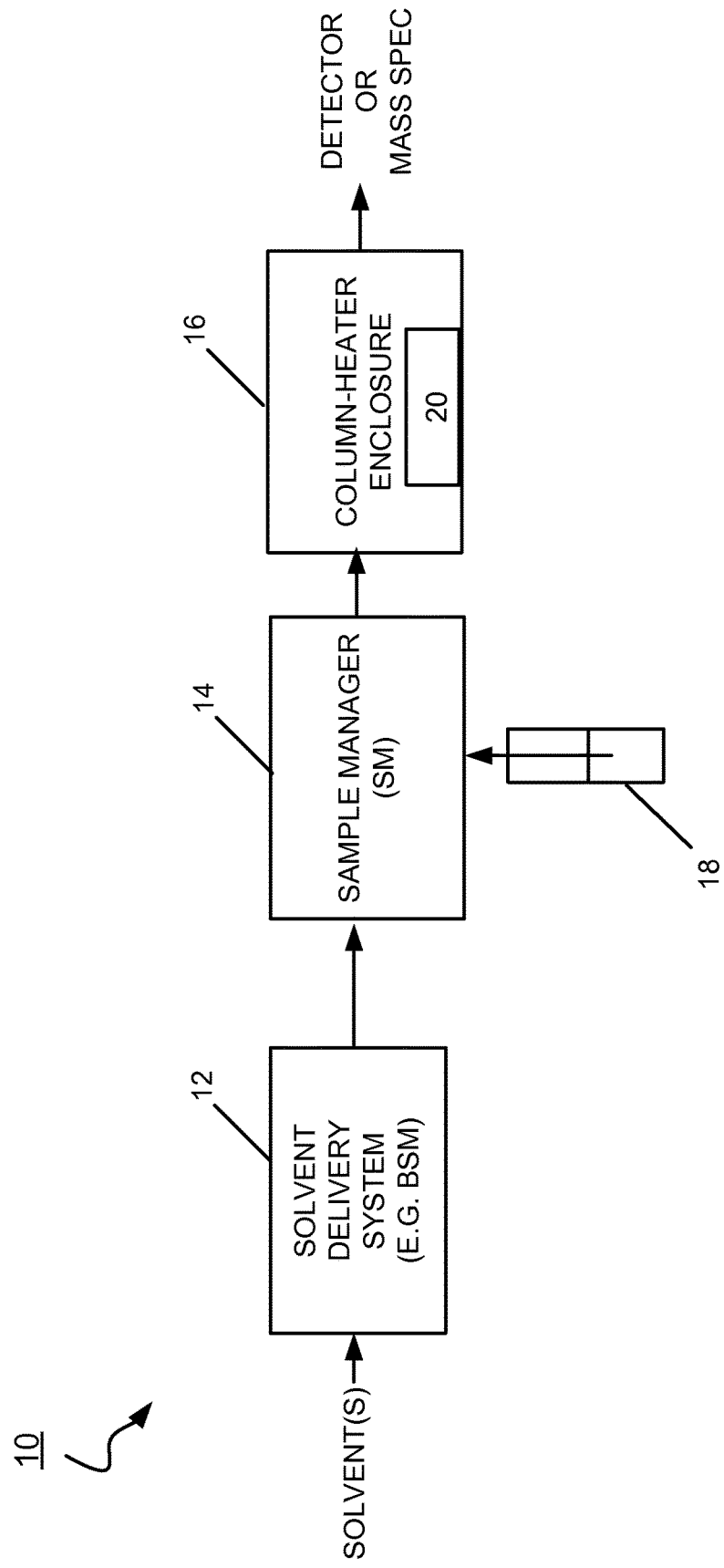
FIG. 1 is a functional block diagram of an embodiment of a liquid chromatography system including a column-heater enclosure having a thermal module with an active pre-heater assembly.

FIG. 1 shows an implementation of a liquid chromatography system 10 for separating a sample into its constituents. The liquid chromatography system 10 includes a solvent delivery system 12 in fluidic communication with a sample manager 14. Generally, the solvent delivery system 12 includes pumps (not shown) in fluidic communication with solvent reservoirs from which the pumps draw solvents. The solvent delivery system 12 delivers a mixture of solvents to the sample manager 14. The sample manager 14 is in fluidic communication with a sample source 18 from which the sample manager acquires and introduces a sample to the solvent mixture arriving from the solvent delivery system 12.

In fluidic communication with the sample manager 14 is a column-heater enclosure 16 for receiving therefrom the solvent composition containing the sample. The column-heater enclosure 16 includes a thermal module 20 for providing a controlled temperature environment for a liquid chromatography column used in separating sample-solvent compositions. As described herein, the thermal module 20 includes an active pre-heater assembly for controlling the temperature of the fluidic sample composition before it enters the column. From the column-heater enclosure 16, the constituents of the separated sample pass to a detector or other equipment, for example, a mass spectrometer, for analyzing the separation.

Figure 2:
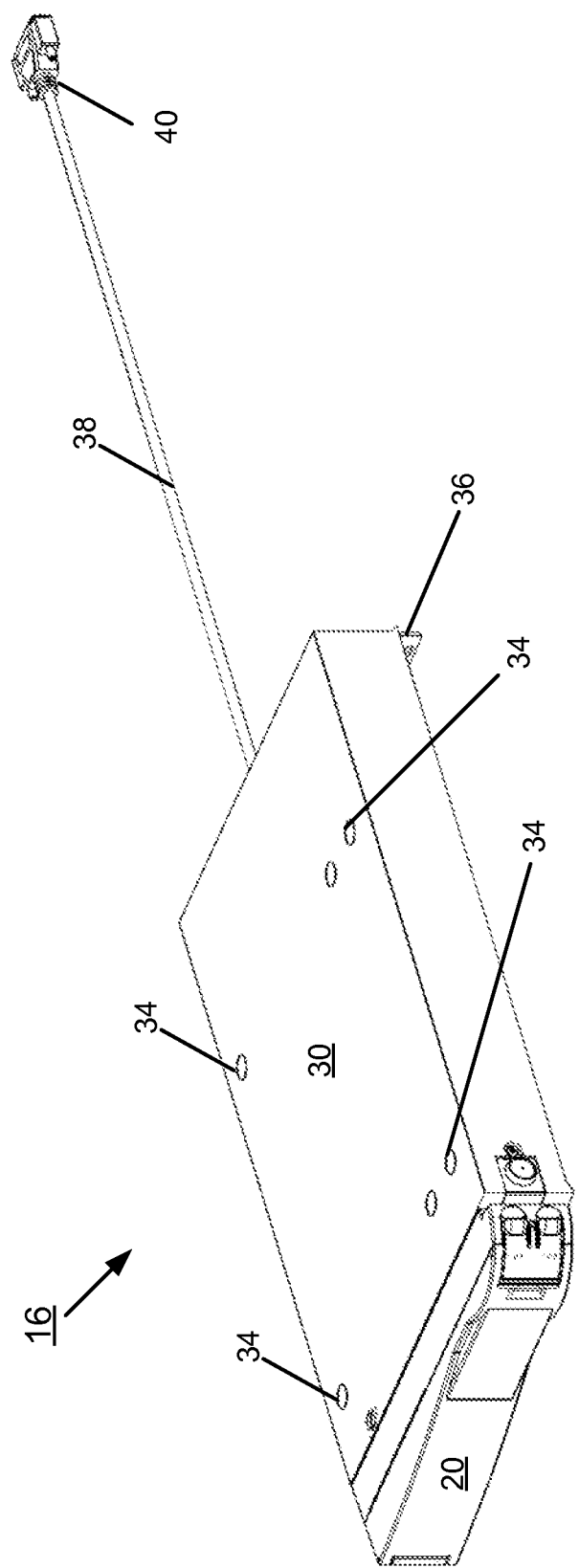
FIG. 2 is an isometric view of an embodiment of the column-heater enclosure with the thermal module.

FIG. 2 shows an implementation of the column-heater enclosure 16 including the thermal module 20, which is attached to a front side of a main housing 30.

Typically, the pieces of equipment, namely the solvent delivery system 12, solvent manager 14, and column-heater enclosure 16, can be vertically stacked. Such an arrangement can help shorten the length of the plumbing between the pieces of equipment. Other pieces, for example, mass spectrometers, because of their size, are often placed to one side of or in front of an equipment stack.

A role of the main housing 30 is to provide support for another piece of equipment, such as a detector, placed on top of the column-heater enclosure 16. The top surface of the housing 30 has dimples 34, for receiving the feet of the enclosure situated above. The dimples 34 align with structural columns within the housing 30 that support the borne weight. The column-heater enclosure 16, itself, can sit physically atop another piece of equipment, such as the sample manager 14. A flange 36 with openings for mechanical fasteners extends orthogonally from the base of the housing 30 and is for mounting the column-heater enclosure 16 securely to the sample manager 14 situated below. An electrical cord 38 and connector 40 electrically connect the column-heater enclosure 16 to the sample manager 14, from which the column-heater enclosure 16 receives DC power and communications for running the thermal module 20.

Figure 3:
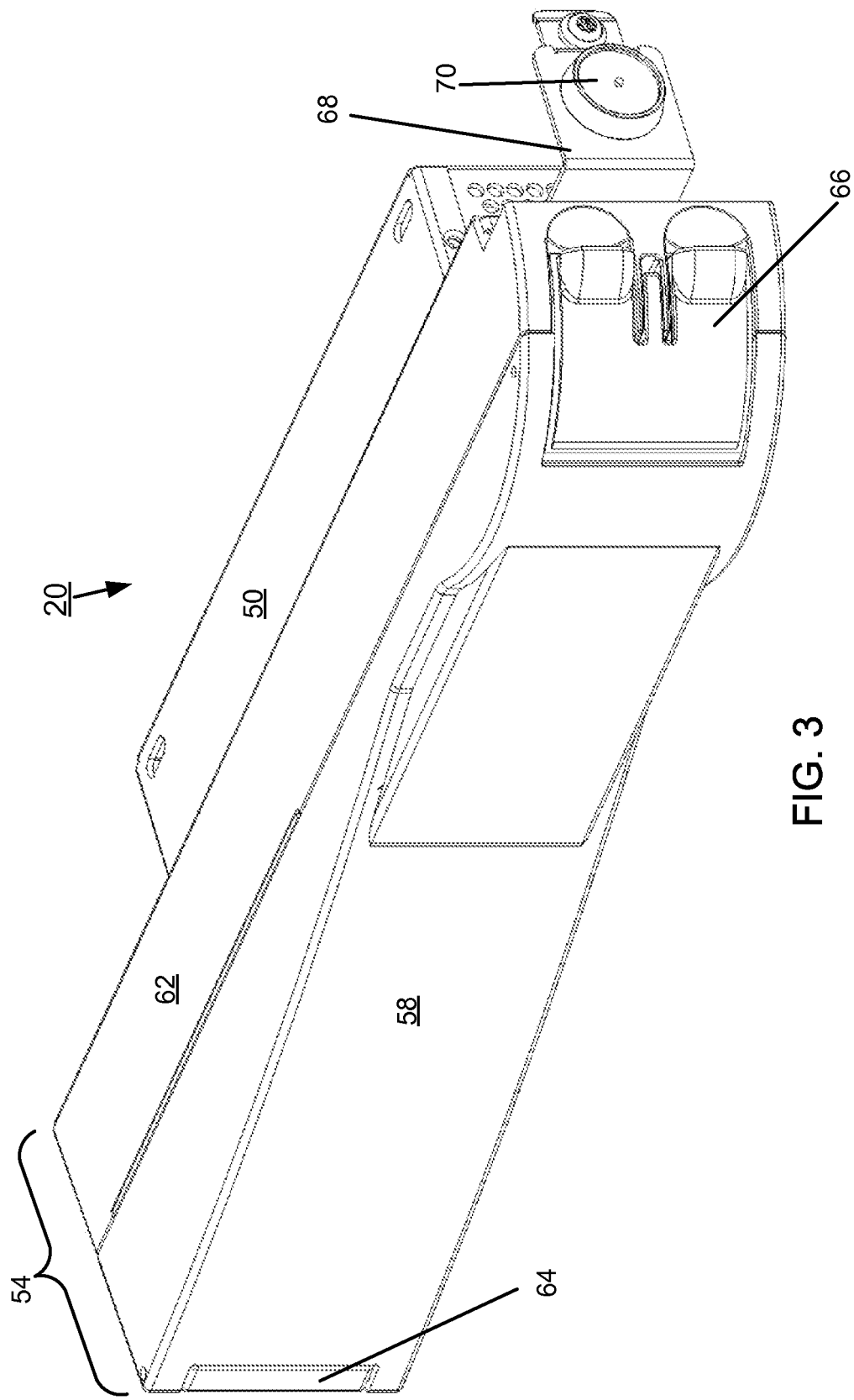
FIG. 3 is an isometric view of the thermal module.

FIG. 3 shows an implementation of the thermal module 20 including an electronics housing 50 coupled to a column housing 54. The column housing 54 comprises a front door 58 coupled at one end to a column holder 62 by a hinge 64 and, at its opposite end, secured in a closed position to the column holder 62 by a (preferably mechanical) latch 66. A bracket 68 extends from one side of the electronics housing 50. The bracket 68 and electronics housing 50 can be made from a single piece of sheet metal. An electrical device 70 is mounted on a surface of the bracket 68. The device 70 is in electrical communication with electronics within the electronics housing 50 and is used to read identification information from some types of chromatography columns.

Figure 4:
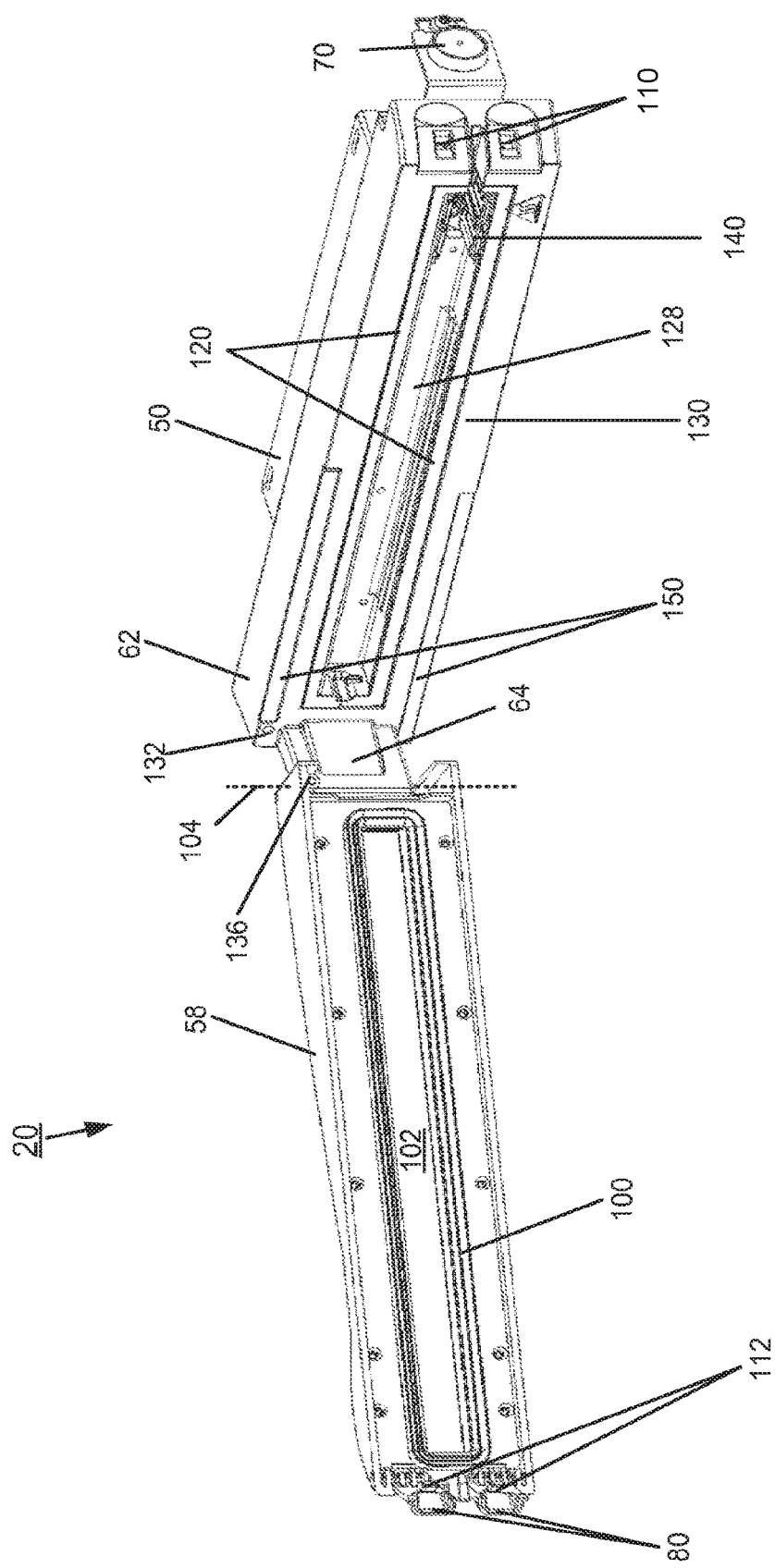
FIG. 4 is an isometric view of the thermal module with its door open.

FIG. 4 shows an isometric view of the thermal module 20 with its front door 58 open to reveal an interior side of the door 58 and the interior of the column holder 62. The interior side of the front door 58 has a generally rectangular rubber gasket 100 disposed near the door's edges. A layer of insulation 102 covers the door interior. A plastic panel (not shown) can be placed over this exposed insulation 102. The door 58 is attached at one end to the hinge 64 for pivoting about axis 104 between an open and closed position. The hinge 64 extends generally orthogonally from a front face 130 of the column holder 62 at one end thereof (opposite the latch end). At the opposite (latch) end of the column holder 62 are a pair of holes 110 for receiving corresponding latch elements 112 on the door 58. These latch elements 112 are interior-side extensions from the raised bumps 80 of the door latch 66 which are unlatched from the holes 110 when pulled upon by a person's fingertips.

The interior of the column holder 62 has an open-faced trough compartment 120, within which is a slidable trough 128. The trough 128 has a back surface and two opposing side surfaces. (The door 58, when closed, provides a fourth side for enclosing the trough compartment 120, the gasket 100 on the door interior pressing against the front face 130 and providing a tight thermal seal around the trough compartment 120.) This trough 128 can be slid to either end of the trough compartment 120, as deemed appropriate when configuring the thermal module 20 for use. Here, the slidable trough 128 is shown positioned at the end of the trough compartment 120 near the hinge 64. At the other end of the trough compartment 120 is a receptacle 140 for receiving an active pre-heater assembly, as describe in more detail below.

The front face 130 of the column holder 62 has a magnetic switch 132 located at the hinge end of the thermal module 20. The magnetic switch 132 detects when a connection is broken between the switch 132 and an opposing magnet 136 on the door 58 (i.e., when the door opens). The thermal module 20 uses signals from the magnetic switch 132 to determine whether to maintain or disconnect power to an active pre-heater assembly installed within the column holder 62.

Figure 5:
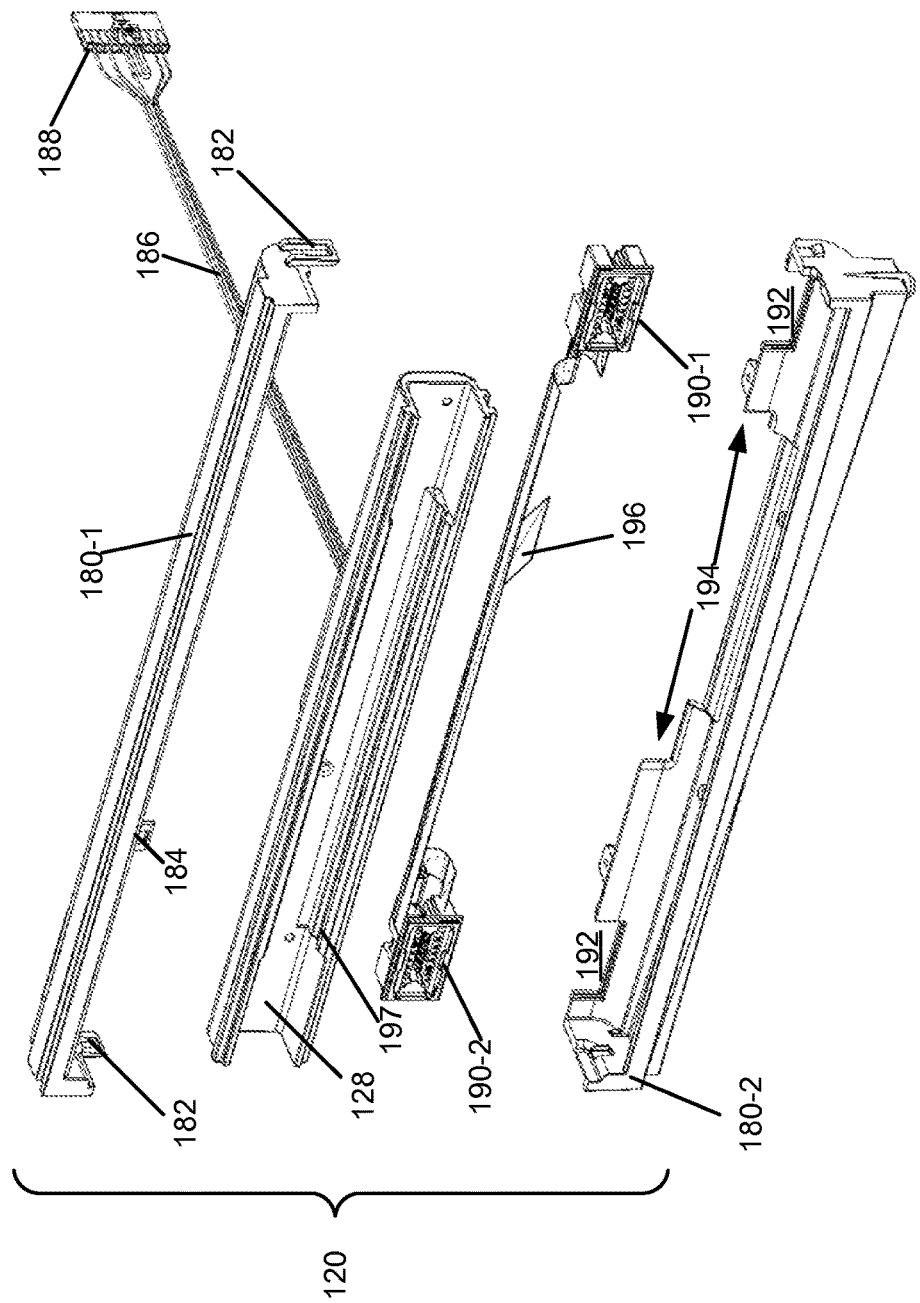
FIG. 5 is an exploded view of a trough compartment within the thermal module.

FIG. 5 shows an exploded view of the trough compartment 120 of the column holder 62. The trough compartment 120 is made of two halves 180-1, 180-2 (generally, 180) held together by two end snaps 182 and a rear snap 184. Mechanical fasteners may also be used to hold the two halves 180 together. Disposed between the two halves 180 is the trough 128 and a pair of electrical sockets 190-1, 190-2 (generally 190) used for electrical connection to an active pre-heater assembly. The sockets 190 sit in appropriately sized rectangular cutout regions 192 in the lower half 180-2 of the trough compartment 120. An electrical ribbon cable 196 is connected between each electrical socket 190 and the electronics within the electronics housing 50 (FIG. 3). The trough 128 can slide to either end of the trough compartment 120 to cover one of the electrical sockets 190.

An electrical cable 186 extends from a rear side of the trough 128 to an electrical connector 188, which plugs into electronics within the housing 50. The electrical cable 186 carries electrical signals for controlling a heater (not shown) and temperature sensor (not shown) mounted to the rear side of the trough 128. The heater is used to heat the trough 128 and the temperature sensor measures temperature of the trough 128. A back surface of the lower half 180-2 of the trough compartment 120 has cutout region 194 to accommodate the cable 186 when the trough 128 slides from one end of the compartment 120 to the other.

Figure 6:
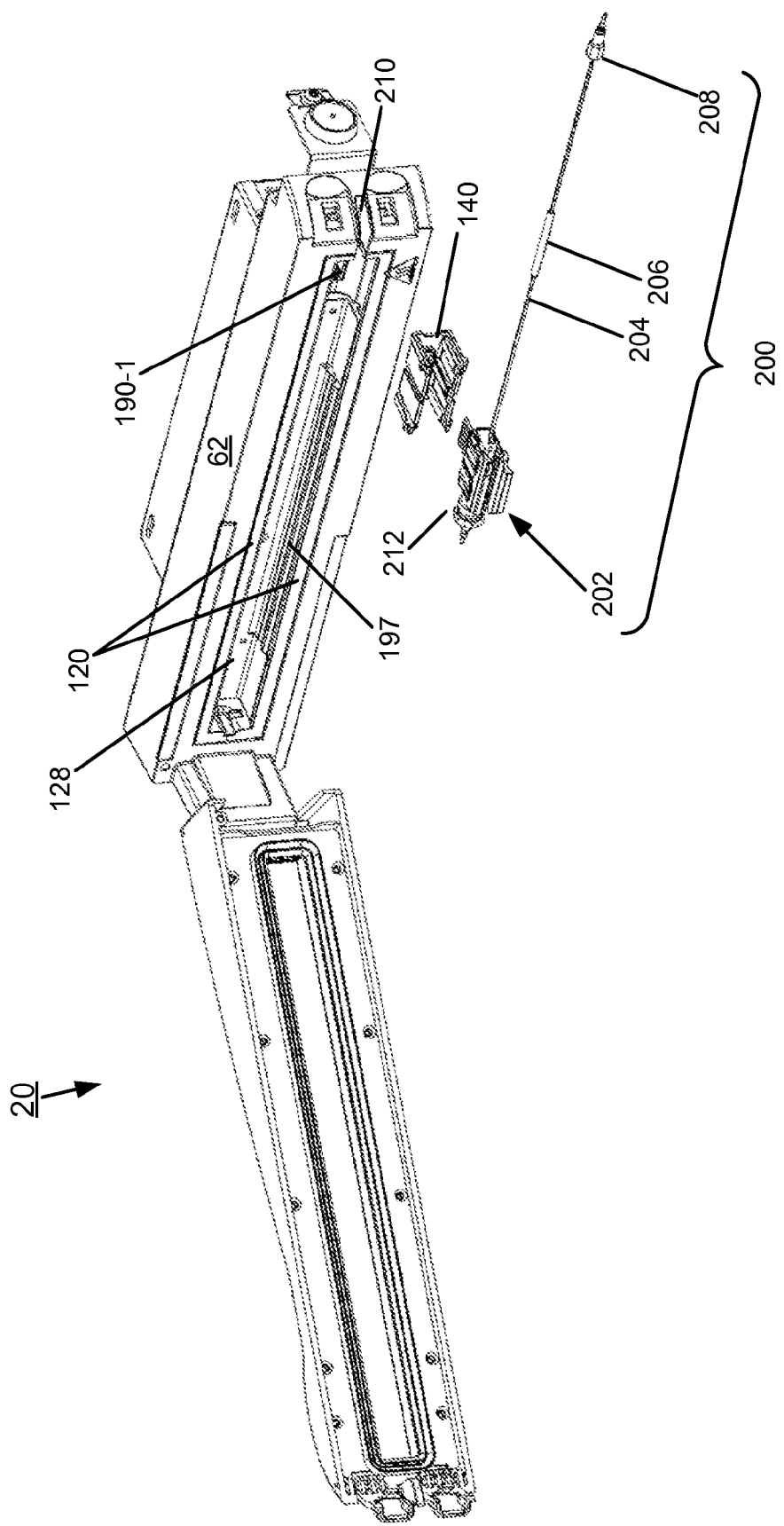
FIG. 6 is an isometric view of a first configuration of the thermal module, including a view of the active pre-heater assembly disposed at a latch end of the thermal module.

FIG. 6 shows an isometric view of the thermal module 20 in a first configuration. The front door 58 of the thermal module is open. An exploded view shows an active pre-heater assembly 200 to include a main heater block assembly 202 with tubing 204 extending from one side thereof. In general, the pre-heater assembly 200 heats liquid before the liquid reaches the column (not shown) residing in the trough 128. In one implementation, the range of temperatures produced by the pre-heater assembly is approximately 4° to 100° C.

Tubing 204 fluidically connects the pre-heater assembly 200 to the sample manager (not shown) for receiving a sample-solvent composition therefrom. A tube sleeve 206 is shrink-wrapped around a section of the tubing 204. Tube fittings 208 are for connecting one end of the tubing 204 to an outlet port the sample manager. Column fittings 212 are for connecting the other end of the tubing 204 to a liquid chromatography column (not shown) disposed within the trough 128.

In the first configuration, the trough 128 in the trough retainer 120 covers the socket 190-2 (FIG. 5) and leaves the other socket 190-1 exposed. The plastic receptacle 140 is shown aligned with the socket 190-1, where the receptacle 140 snaps into the trough compartment 120. The heater block assembly 202 is shown aligned with the receptacle 140, into which the heater block assembly 202 snaps. When the pre-heater assembly 200 is installed in the trough compartment 120, the tubing 204 passes through a slit 210 in the latch side of the column holder 62.

Alternatively, in a second configuration, the trough 128 is slid toward the latch end of the trough compartment 120 such that it covers the socket 190-1 (FIG. 6), and leaves exposed the socket 190-2 at the hinge end of the trough compartment 120.

Figure 7:
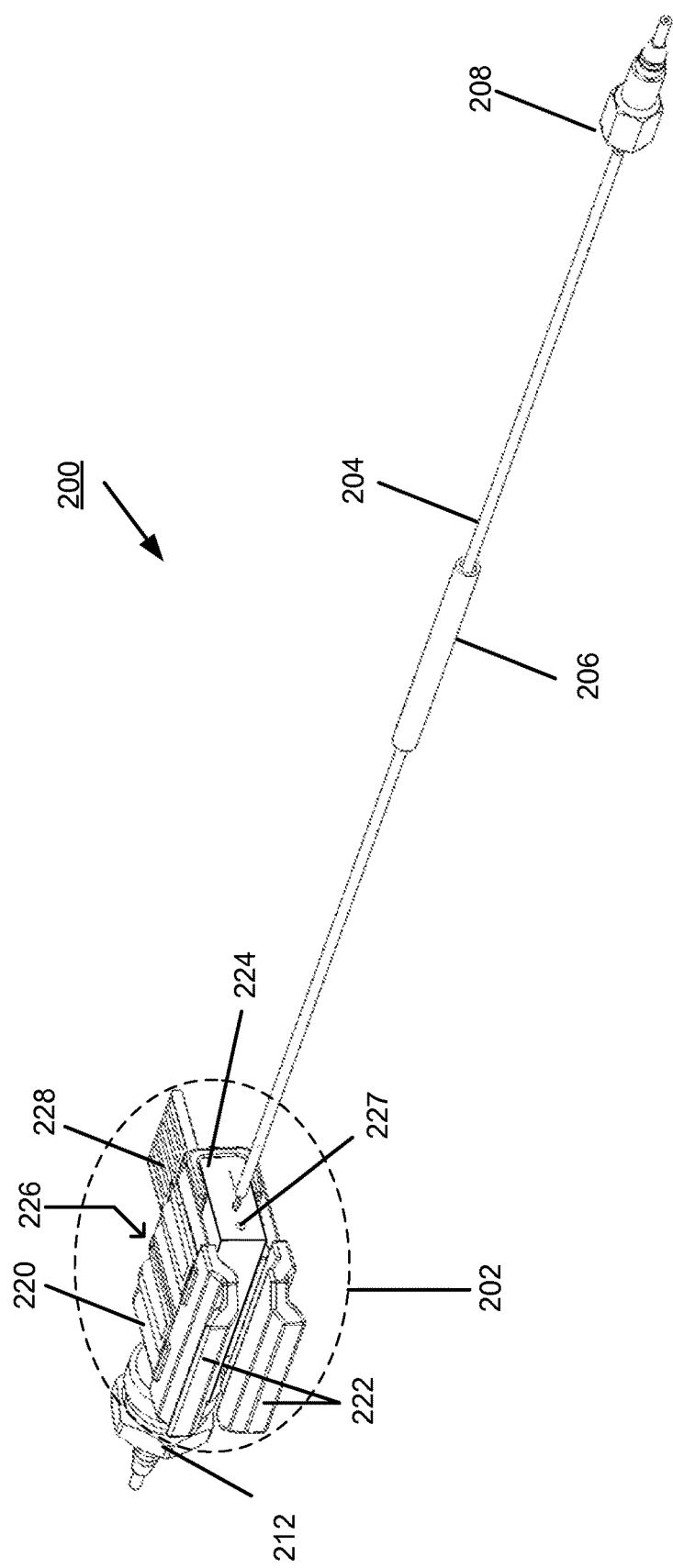
FIG. 7 is an isometric view of an embodiment of the active pre-heater assembly including a heater block assembly with tubing, tube fittings, and column fittings.

FIG. 7 shows an isometric view of an implementation of the active pre-heater assembly 200 including the heater block assembly 202, tubing 204, a tube sleeve 206 shrink-wrapped around a section of the tubing 204, tube fittings 208, and column fittings 212. The heater block assembly 202 comprises a spring carrier 220 made of a pair of opposing prongs 222 spaced apart by a rear wall 226, a heater block 224 disposed between the prongs 222, and a printed circuit board 228 extending from a reverse side of the rear wall 226. The tubing 204 passes into a channel 230 in one side of the heater block 224.

Figure 8A:
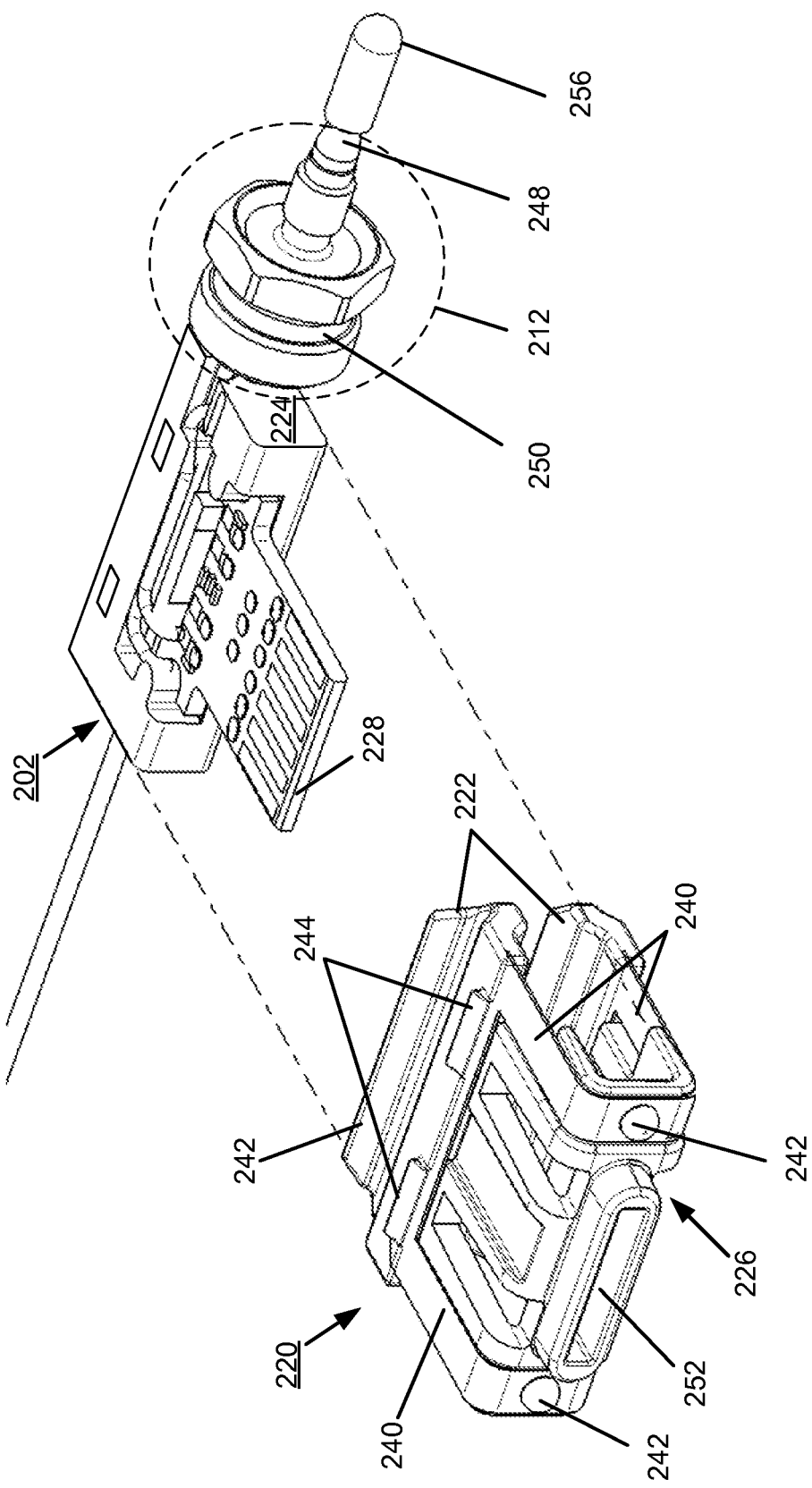
FIG. 8A is an exploded reverse view of the active pre-heater assembly of FIG. 9.
Figure 8B:
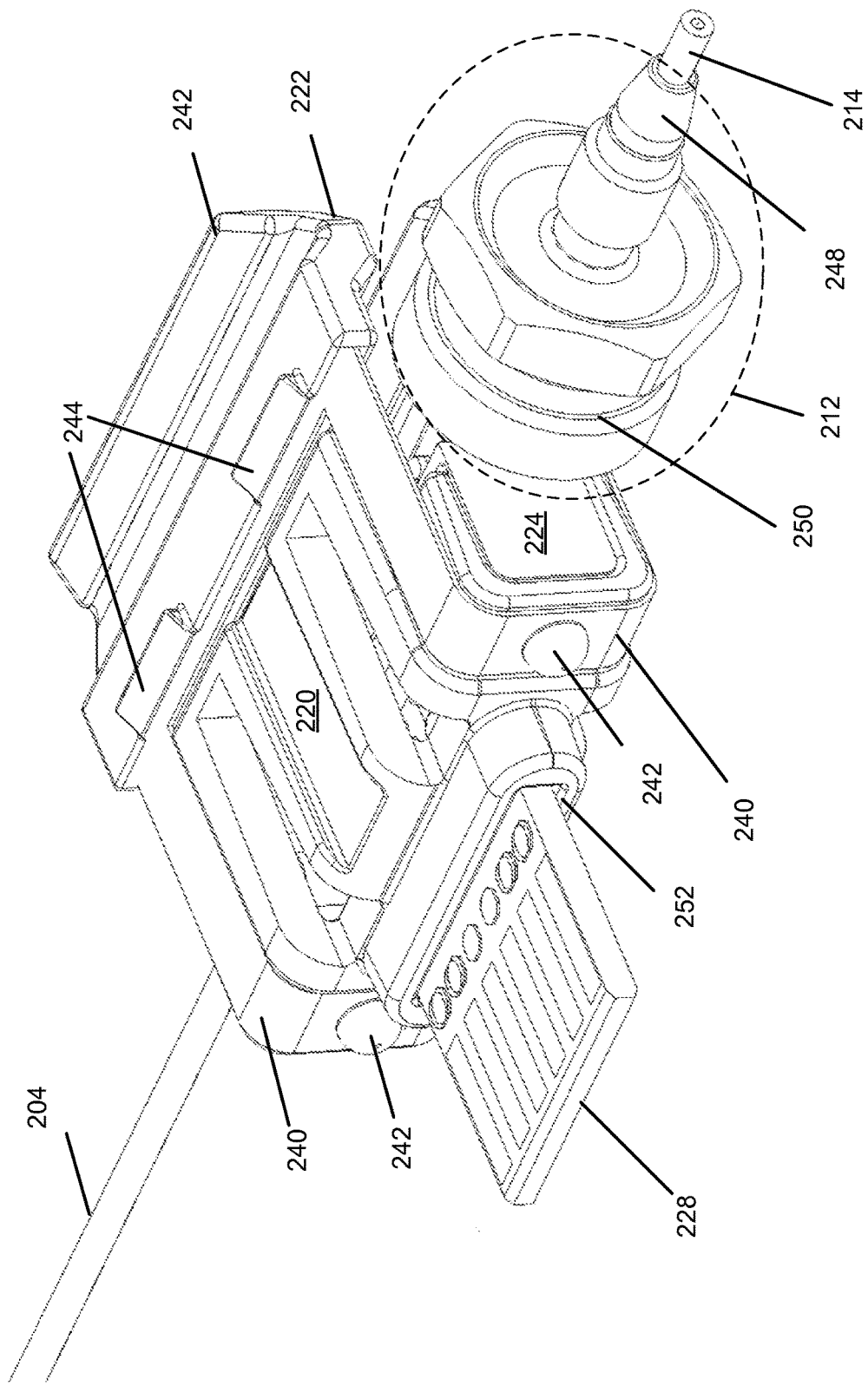
FIG. 8B is a reverse view of the active pre-heater assembly of FIG. 9

FIG. 8A and FIG. 8B are reverse views of the active pre-heater assembly 200: FIG. 8A shows the heater block assembly 202 aligned for coupling to the spring carrier 220 and FIG. 8B shows the heater block assembly 202 joined to the spring carrier 220. The opposing prongs 222 of the spring carrier 220 are integrally formed with a metallic leaf-spring 240. The leaf-spring 240 is a flat, rectangular window of metallic material that is curved into an arcuate shape defined by the prongs 222. The leaf-spring 240 biases the prongs 222 of the spring carrier 220 apart and bends when the prongs 222 are pinched together.

The leaf-spring 240 has openings through which project molded posts 242, which are melted to hold the leaf-spring 240. Each prong 222 of the spring carrier 220 has a pair of raised ramps 244 that snap into openings in interior surfaces of the receptacle 140. A raised edge 242 of each prong 222 provides a finger grip that a user can use to pinch the prongs 222 together in order to decouple the ramps 244 from the receptacle 140 so that the spring carrier 220 can be removed. The printed circuit board 228 of the heater block assembly 202 is aligned to project through a rear side opening 252 in the rear wall 226 of the spring carrier 220.

In one implementation, the column fittings 212 include a ferrule 248, slipped over the tubing 204, and an adjustable biasing element 250 for urging the ferrule 248 and the tip of the tubing 204 (here, with a shipping cap 256 to be removed upon installation) into a corresponding inlet port of the liquid chromatography column.

Figure 9:
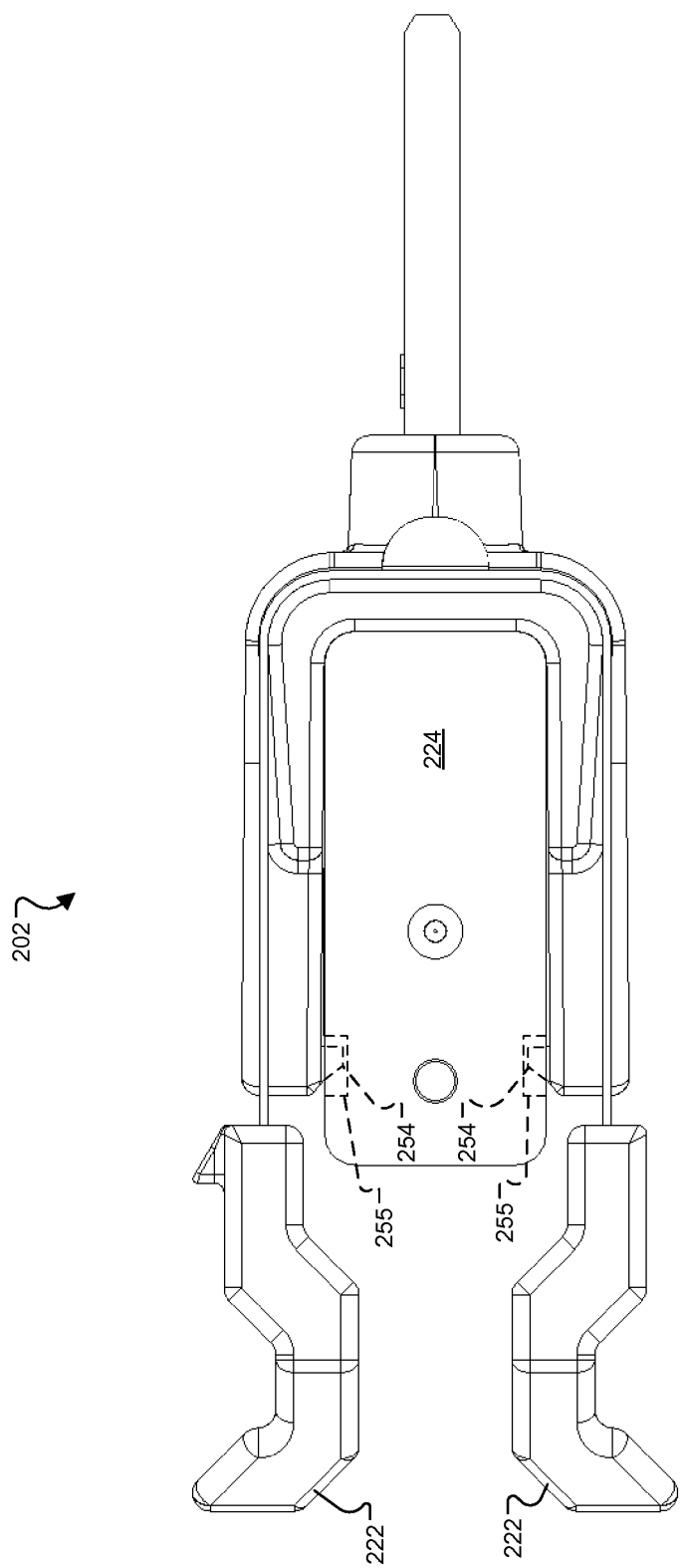
FIG. 9 is a side view of the heater block assembly.

FIG. 9 shows a side view of the heater block assembly 202 of the active pre-heater assembly 200 with the heater block 224 disposed between the prongs 222 of the spring carrier 220 and being held in place by snap features 254 extending from an interior surface of the prongs 222 which engage recesses 255 (see also FIG. 11A) that are formed in the surface of the heater block 224. Hardware is omitted from FIG. 9 for clarity. The heater block 224 is made of a zinc alloy, such as ZAMAK 3, or of aluminum, or of some other thermally conductive alloy.

Figure 10:
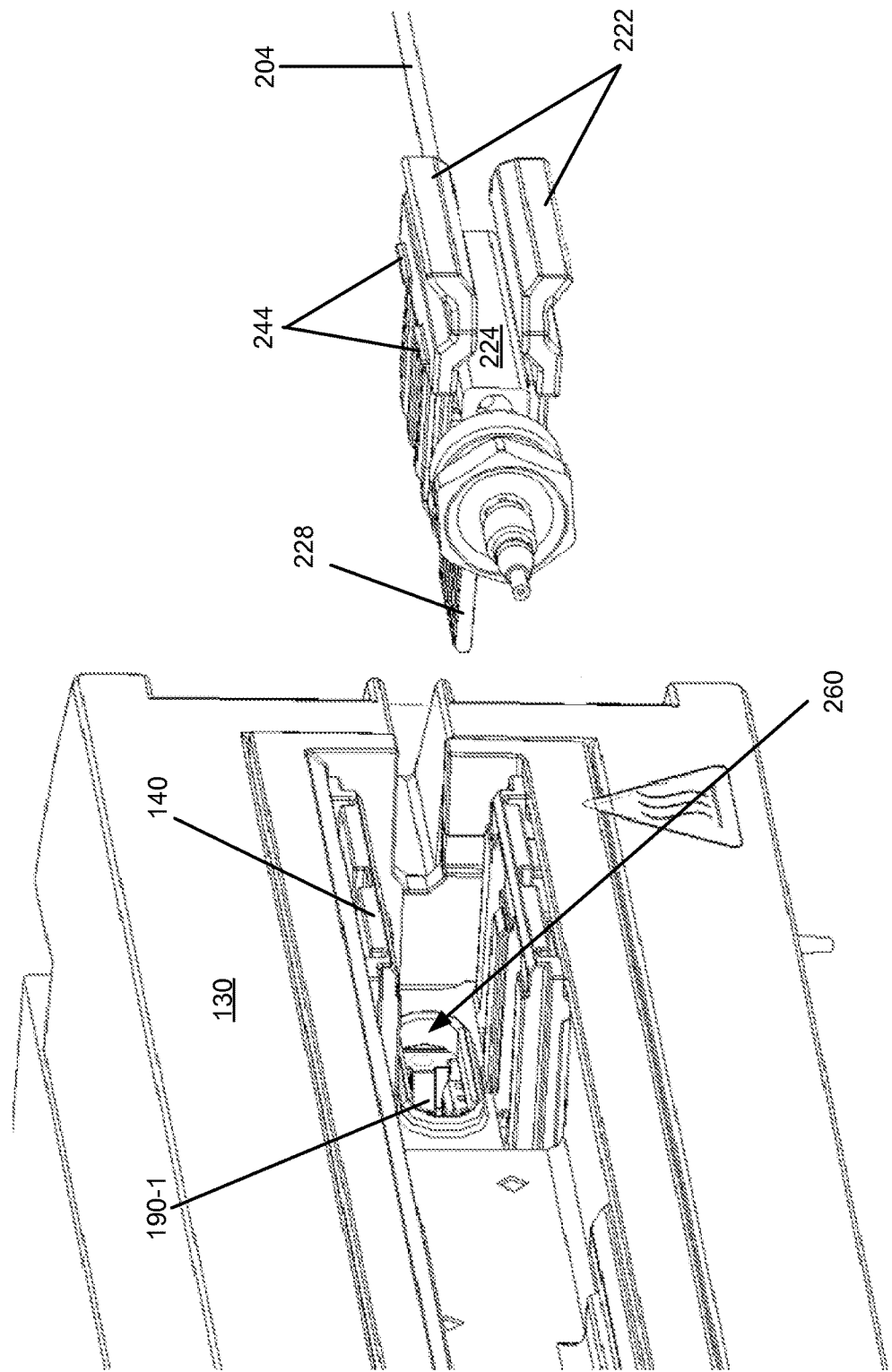
FIG. 10 is side view of the active pre-heater assembly positioned to enter a receptacle installed within the trough compartment.

FIG. 10 shows an exploded view of the active pre-heater assembly 200 positioned for insertion into the receptacle 140, which is here installed in front of the socket 190-1 of the trough compartment 120 of the column holder 62. The circuit board 228 is aligned for entry into an opening 260 in the crook of the receptacle 140. When the pre-heater assembly 200 is fully installed, the circuit board 228 penetrates this opening 260 and plugs into the electrical socket 190-1 situated behind the receptacle 140.

Figure 11A:
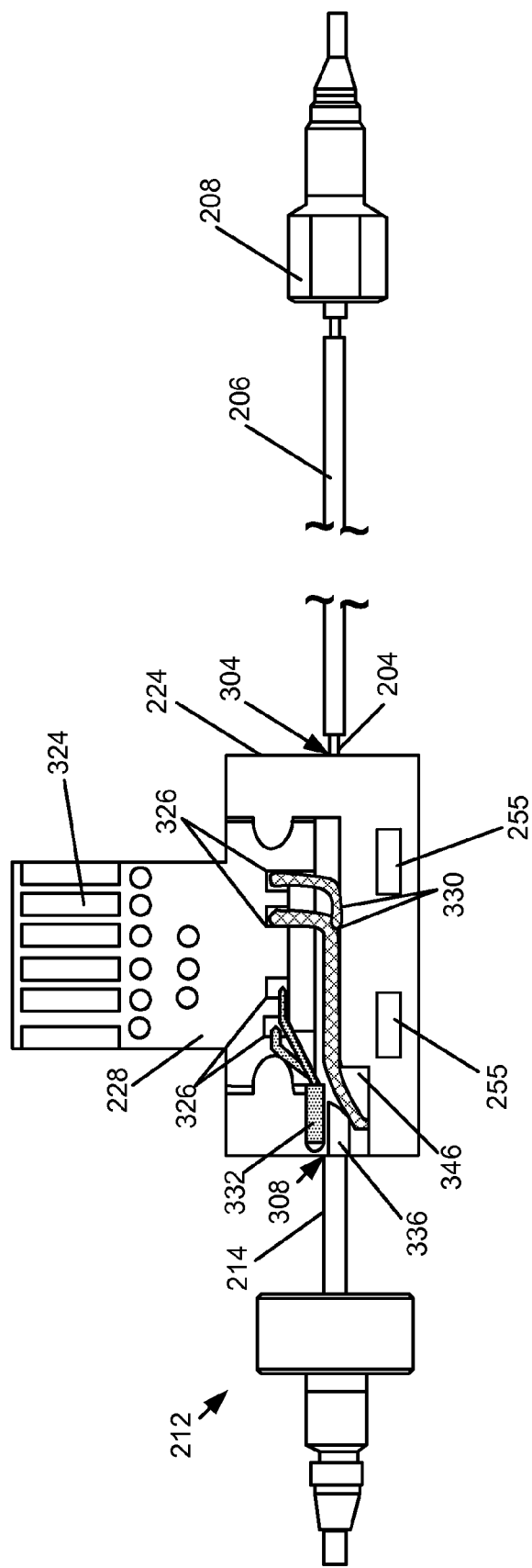
FIG. 11A is an elevated view of the active pre-heater assembly without the spring carrier.
Figure 11B:
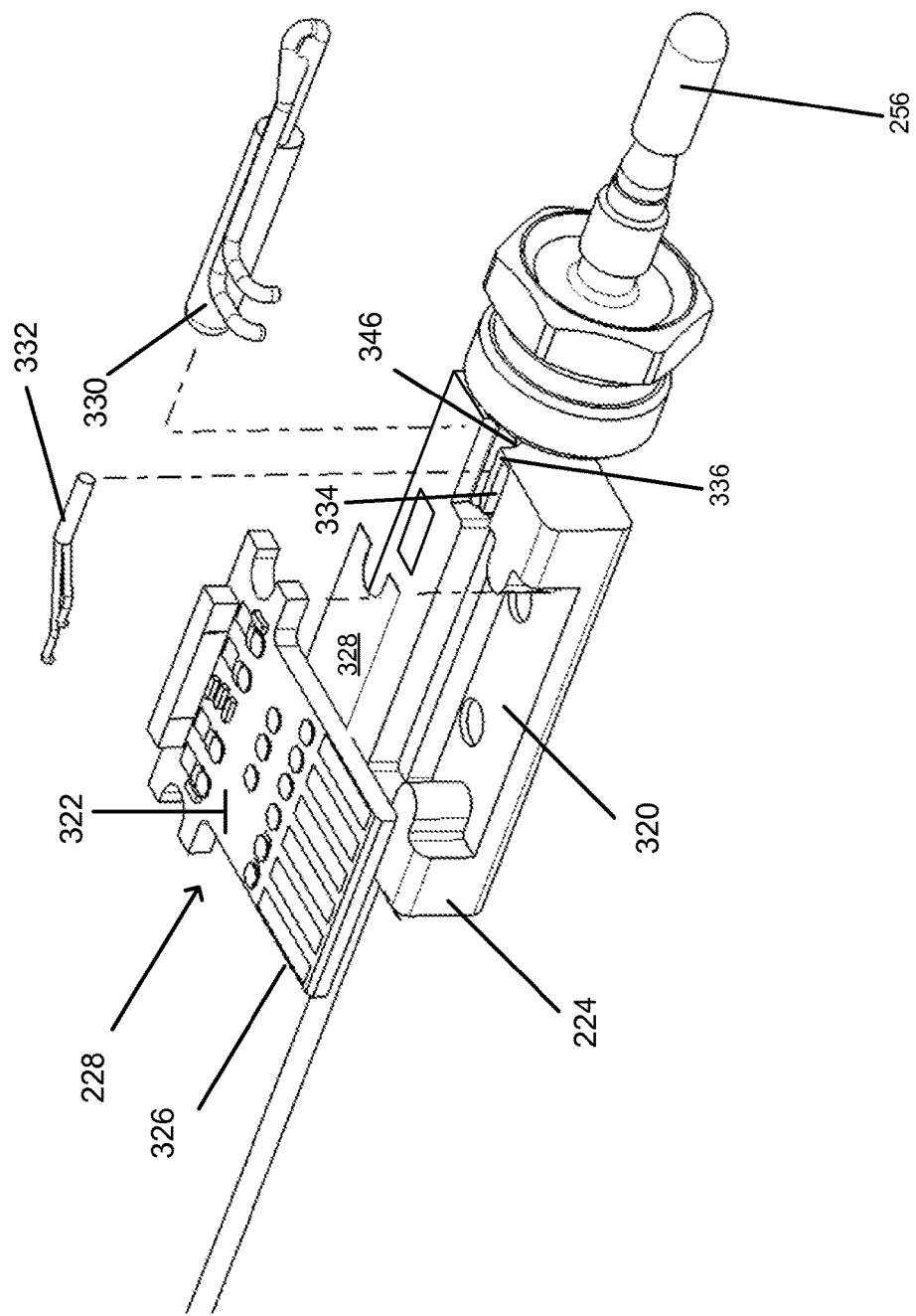
FIG. 11B is an exploded view of the active pre-heater assembly without the spring carrier.

FIG. 11A and FIG. 11B show an embodiment of the active pre-heater assembly 200 without the spring carrier 220 (FIG. 10A). FIG. 11A is an isometric view and FIG. 11B is an exploded view. The heater block 224 has a major cavity 320 (FIG. 11B). The printed circuit board 228 has a contour that fits closely into this cavity 320. An upper surface 322 of the circuit board 228 has contact fingers 324 and electrical contact pads 326. A portion of the printed circuit board 228 with the contact fingers 324 extends from and overlaps the heater block 224. A thin insulation layer 328, also having a contour shaped to fit closely into this major cavity 320, is disposed between the circuit board 228 and the heater block 224, to prevent the circuit board 228 from shorting to the metal heater block 224.

A heater cartridge 330 resides in a cavity 346 in the heater block 224. Two wires of the heater cartridge 330 connect to two of the electrical pads 326 on the upper surface 322 of the circuit board 228. A temperature sensor 332 (preferably, a thermistor) is placed within another cavity 334 of the heater block 224, a thin wall 336 separating the temperature sensor 332 from the heater cartridge 330 to avoid direct contact therewith. Circuitry on the circuit board 228 uses the temperature measured by the temperature sensor 332 to limit the operation of the heater cartridge 330 and thus the maximum temperature reached by the heater block 224. Other circuitry on the circuit board 228 includes a fuse wired in series with the heater cartridge 330, which disconnects the heater cartridge from power in the event of malfunction. A thermal epoxy fills the cavities 320, 334, 346, to cover and protect the heater cartridge, temperature sensor 332, and various electrical components on the circuit board 228 and to provide for heat transfer. A vent hole 227 (FIG. 7) is provided which extends from the inlet end of the heater block 224 and into the cavity 346, which allows air in the cavity 34 to vent as it is filled with the epoxy.

Figure 12:
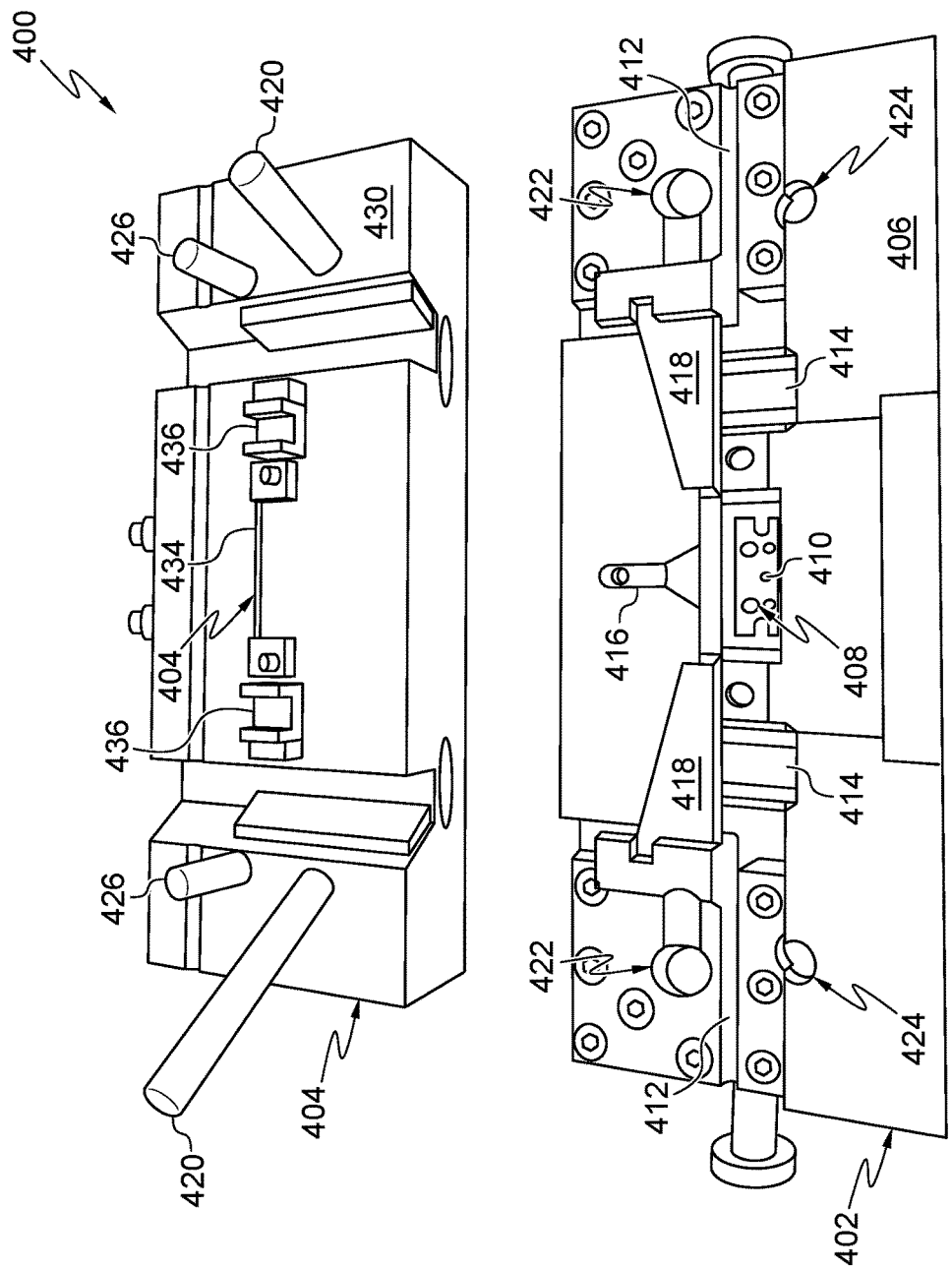
FIG. 12 is a perspective view of a die cast tool.

The heater block 224 can be formed around the tubing 204 in an insert cast (die-casting) process. The use of the insert cast process for forming the heater block 224 can significantly improve manufacturability and reduce lead times and design costs as compared to prior known methods that include soldering tubing into a metal block. FIG. 12 shows a die cast tool 400 for performing the casting process. The tool 400 includes a first, stationary tool portion 402 and a second, movable tool portion 404. The stationary and movable tool portions 402, 404 are formed from material or materials capable of withstanding the pressures and temperatures of the die casting process, such as hardened steel.

The stationary tool portion 402 includes a stationary tool body 406 which defines a first block cavity 408. The first block cavity 408 helps to form the geometry of heater block 224. A first locating pin 410, and features for forming the recesses 255 (FIG. 11A) in the heater block 224 are disposed within the first block cavity 408. The stationary tool body 406 also defines a pair of grooves 412 for receiving a tubing assembly 500 (FIG. 13) and a pair of V alignment blocks 414. The grooves 412, the V alignment blocks 414 and the first locating pin 410 help to position the tubing assembly 500 relative to first block cavity 408. A sprue hole 416 in the stationary tool body 406 allows molten metal to be delivered toward the first block cavity 408.

The stationary tool portion 402 also includes a pair of slides 418. The slides 418 include features for forming the heater cartridge cavity 346 and a vent hole 227 (FIG. 7) along the sides of the heater block 224. The slides 418 are displaceable along the stationary tool body 406, and their movement is actuated by drive posts 420 in the movable tool portion 404. The drive posts 420 are received in through holes 422 in the stationary tool body 406. The drive posts 420 engage and displace the slides 418 as the drive posts 420 pass through the through holes 422. Alignment holes 424 are provided in the stationary tool body 406 for receiving alignment posts 426 of the movable tool portion 404 to align the stationary and movable tool portions relative to each other.

The movable tool portion 404 includes a movable tool body 430 which defines a second block cavity 432. The first and second block cavities 408, 432 and the slides 418 together form the geometry of the heater block 224. A second locating pin 434 and features for forming the recesses 255 (FIG. 11A) on the side of the heater block 224 are disposed within the second block cavity 432. The first and second locating pins 410, 434 together help to position a tubing assembly 500 (FIG. 13) relative to the first and second block cavities 408, 432 so that molten metal flows around the tubing assembly 500 in such a manner as to form a die-cast heater block 225 that encases the tubing assembly 500.

The movable tool portion 404 also includes a pair of V alignment blocks 436 that include protrusions which are received within recesses in the V alignment blocks 436 on the stationary tool portion 402 to assist in alignment and positioning of the tubing assembly 500.

Figure 13:
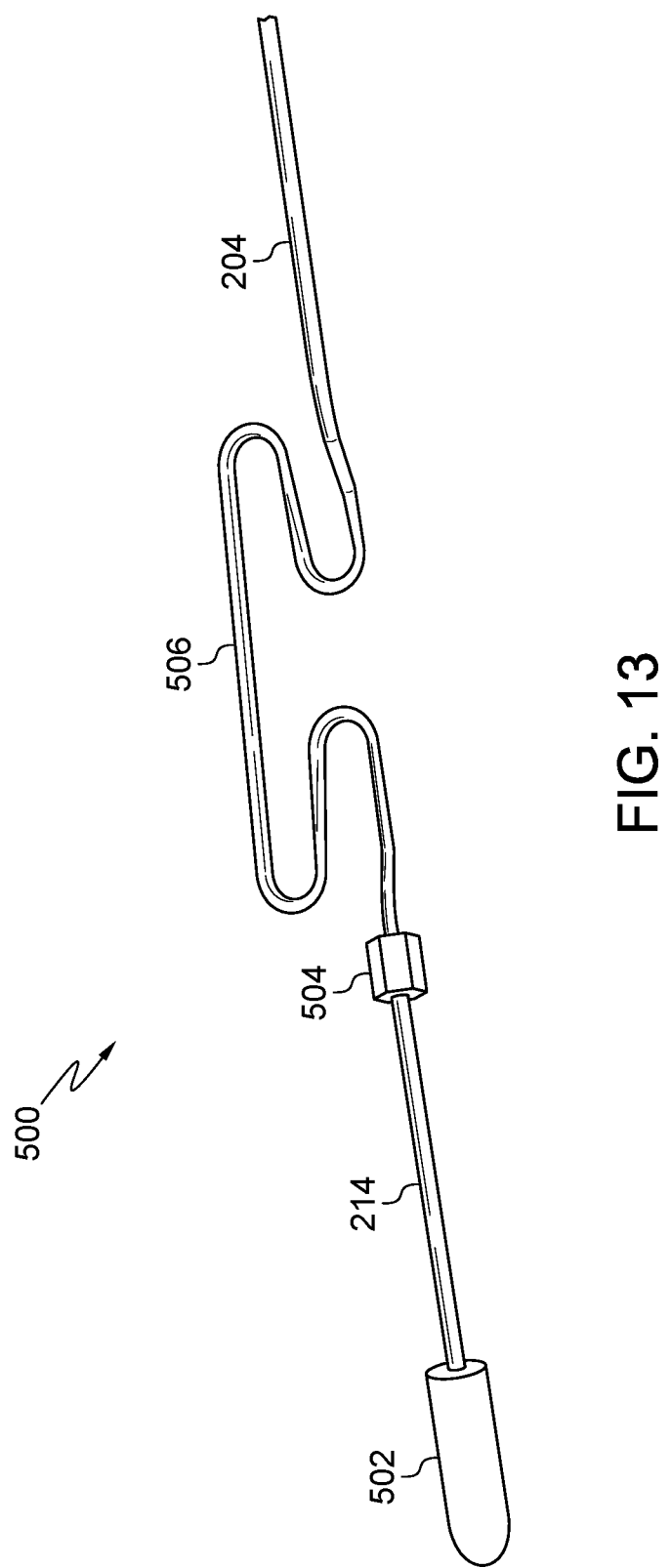
FIG. 13 is a perspective view of a solvent tubing assembly.

An insert cast assembly process begins with a solvent tubing assembly 500, as shown in FIG. 13. The solvent tubing assembly 500 comprises the tubing 204; the metal tube sleeve 214 (shown with a shipping cap 502); and a restraining component 504. The metal tube sleeve 214 is welded around the tubing 204, and the restraining component 504 is welded around the metal tube sleeve 214. The tubing 204 is formed of metal (e.g., stainless steel) and has an inside diameter of about 0.003 inches to about 0.007 inches and an outside diameter (OD) of approximately 0.025 inches or less. The tubing 204 includes a serpentine loop 506 which provides a fluid path through the heater block 224. The metal tube sleeve 214 is formed of stainless steel and has an inner diameter of about 0.026 inches and an outer diameter of about 0.063 inches. In the example depicted in FIG. 13, the restraining component 504 is a hexagonally shaped stainless steel sleeve that is welded about the end of the metal tube sleeve 214. The restraining component 504 helps to inhibit (e.g., prevent) the tubing 204 from rotating within the heater block 224.

Figure 14:
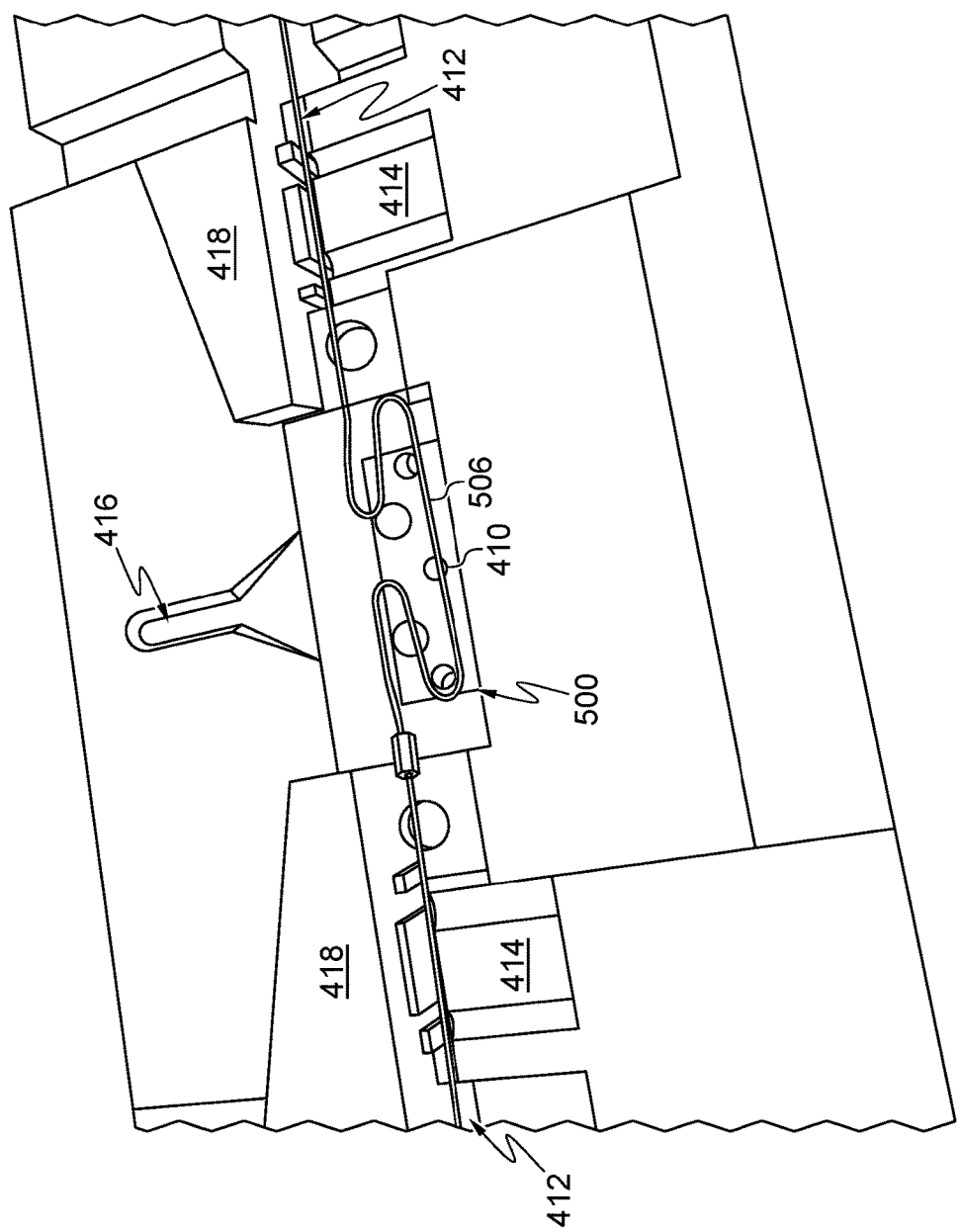
FIG. 14 is a perspective view of the solvent tubing assembly of FIG. 13 arranged in a stationary tool portion of the die cast tool of FIG. 12.

With reference to FIG. 14, the tubing assembly 500 is inserted into the stationary tool portion 402 and is located by the V alignment blocks 414 and the first locating pin 410. The first locating pin 410 receives the serpentine loop 506 and helps to ensure that the tubing 204 is surrounded by metal during the casting process. The grooves 412 in the body and the V alignment blocks 414 receive the tubing 204 and the tube sleeve 214.

The movable tool portion 404 (FIG. 12) is then slid into place atop the stationary tool portion 402, and molten metal (e.g., zinc alloy (ZAMAK 3), aluminum, etc.) is then injected into the tool 400 via the sprue hole 416 in the stationary tool portion 402. The molten metal fills the region between the first and second block cavities 408, 432 to form the heater block 224, which encases the restraining component 504 and the serpentine loop 506.

Figure 15:
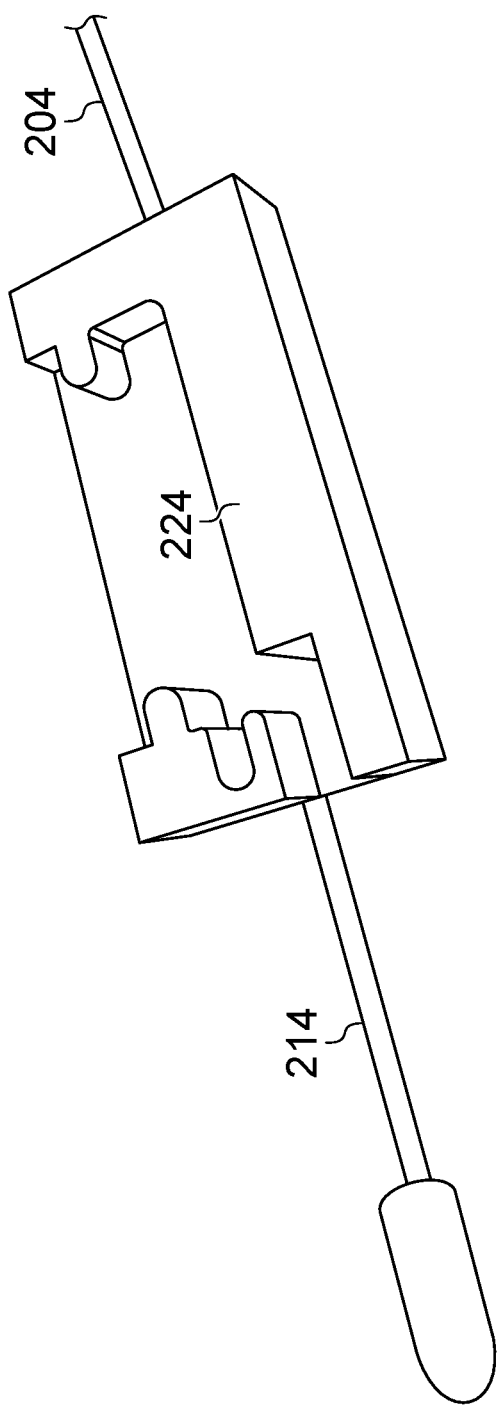
FIG. 15 is a perspective view of an insert cast assembly.

Referring to FIG. 15, the finished insert cast assembly is a single inseparable unit that comprises the tubing 204, tube sleeve 214, the restraining component 504 (embedded in the heater block 224, and, thus, not visible in FIG. 15), and the heater block 224.

Figure 16:
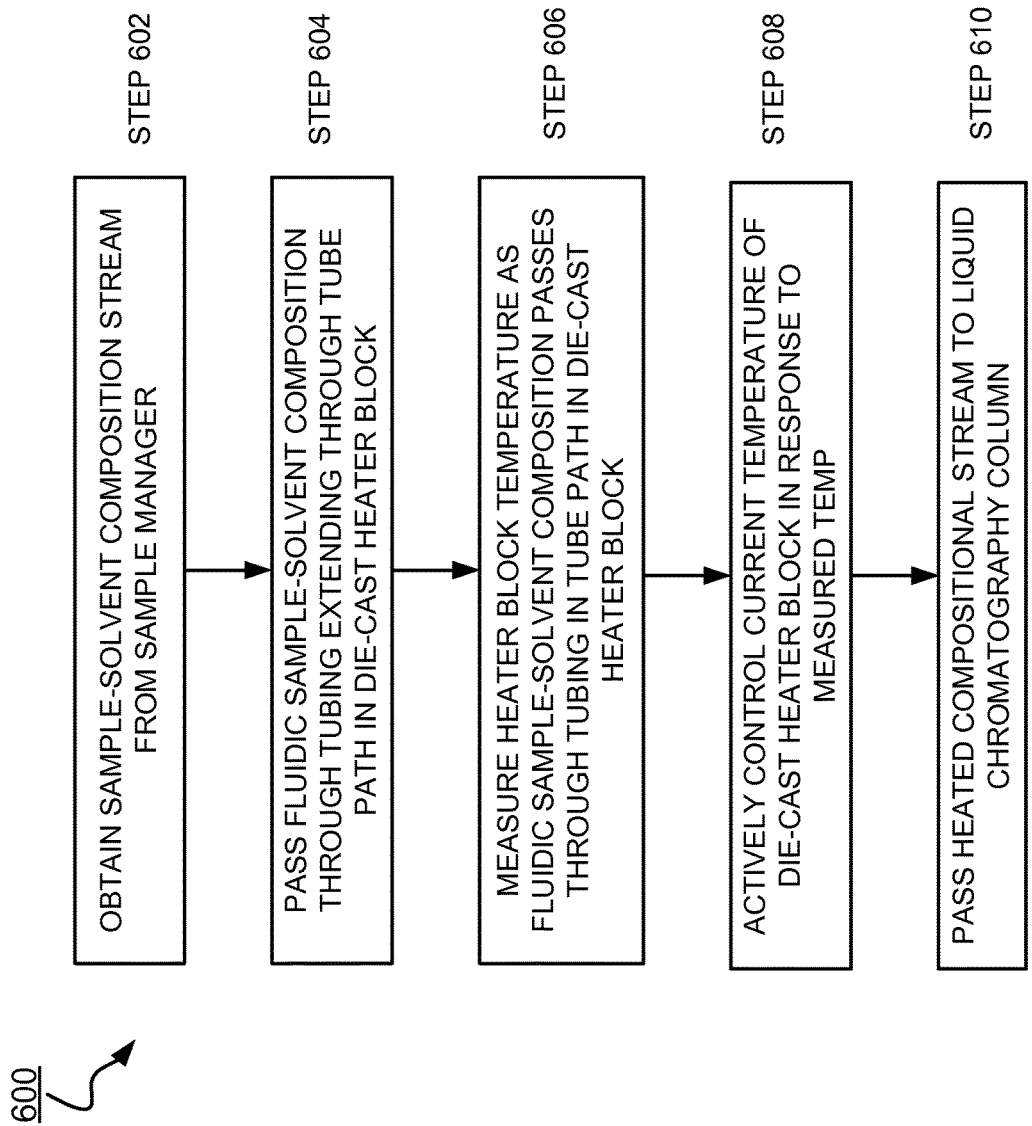
FIG. 16 is a flow diagram of an embodiment of a process of pre-heating a liquid flowing into a liquid chromatography column.

FIG. 16 shows an implementation of a process 600 of pre-heating a flowing liquid before the liquid enters a liquid chromatography column. At step 602, a sample-solvent composition stream is received. This sample-solvent composition stream is passed (step 604) through tubing extending through a tube path in a heater block assembly. The tubing is in thermally conductive contact with a heater block of the heater block assembly. The heater block is die-cast from thermally conductive material such that heat transfers from the heater block to the sample-solvent composition stream as the sample-solvent composition stream passes through the tubing. A current temperature of the heater block is dynamically measured (step 606) as the sample-solvent composition stream passes through the tubing. The current temperature of the heater block is actively controlled (step 608) in response to the dynamic measurement. The heated sample-solvent composition stream is moved out (step 610) of the heater block into a liquid chromatography column.

Figure 17:
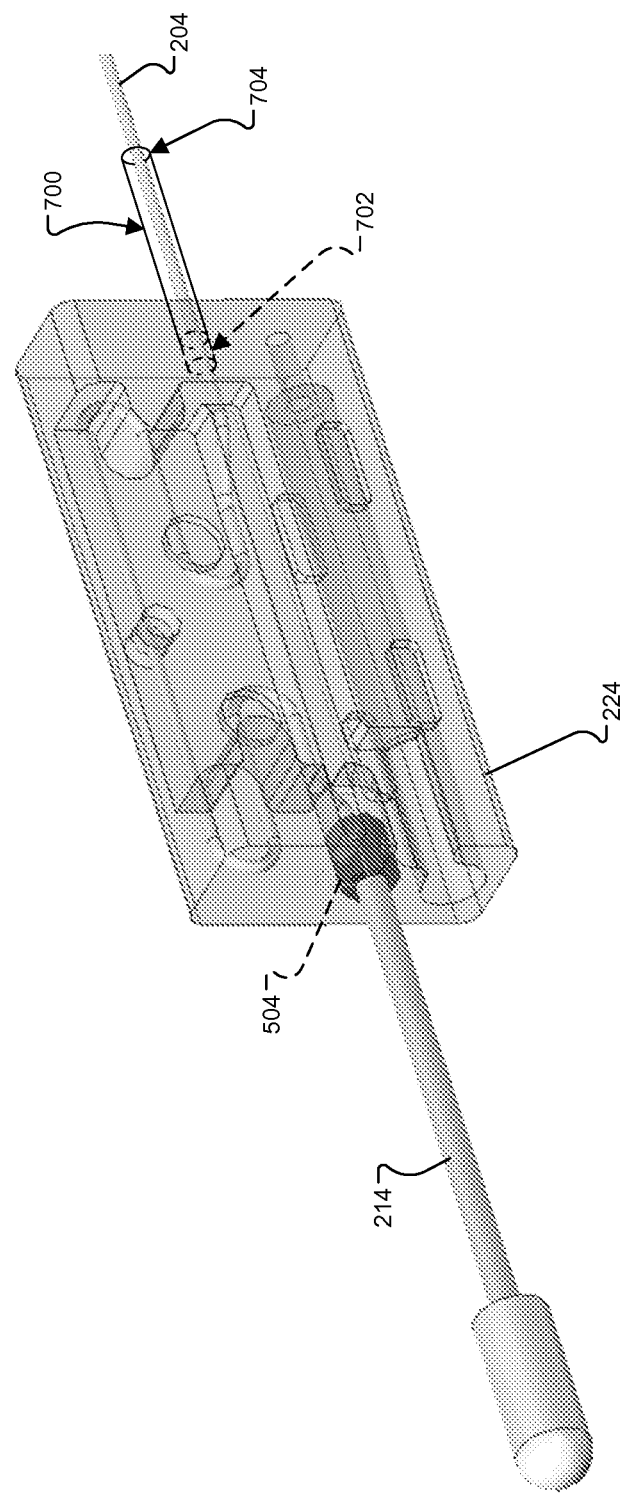
FIG. 17 is a perspective view of an implementation of an insert cast assembly having a strain relief component.

Although a few implementations have been described in detail above, other modifications are possible. For example, some implementations may include strain relief component at the inlet end of the heater block, which can help to increase the bend radius of the tubing 204 for reduced fatigue at the inlet end. FIG. 17 illustrates an implementation of the insert cast assembly in that includes a strain relief component 700. The strain relief component 700 may comprise a tension coil spring disposed about the tubing 204, or a section of polymeric material (e.g., polyether-ether-ketone tubing) disposed (e.g., coated, wrapped, slid over) the tubing at the inlet end of the heater block 224. The strain relief component 700 can be positioned about (e.g., slid over) the tubing assembly 500 prior to the insert casting process such that, in the finished assembly, a first end portion 702 of the strain relief component 700 is encased in the heater block 224 and forms part of the inseparable unit, while a second end portion 704 of the strain relief component 700 extends outwardly from an inlet end of the heater block 224.

In addition, although described with respect to liquid chromatography (e.g., HPLC, UPLC) applications, the principles can be implemented in other types of applications for which pre-column heating of a mobile phase fluid is desired. For example, the active pre-heater assembly comprising the heater block described herein can also be utilized for pre-column heating of a mobile phase fluid flow in a supercritical fluid chromatography (SFC) system.

While an implementation has been described in which the tubing includes a serpentine loop, in some cases the tubing passes through the heater block in a straight path.

Accordingly, other implementations are within the scope of the following claims.

What is claimed is:

1. An apparatus for heating a flowing fluid, comprising:
    a tubing assembly comprising:
        tubing;
        a tube sleeve welded around the tubing; and
        a restraining component welded around the tubing;
    a heater block made of thermally conductive material;
    a heater cartridge in thermal communication with the heater block, the heater cartridge configured to provide heat to the heater block for transfer to fluid flowing through the tubing assembly;
    a strain relief component disposed about the tubing and comprising a polymeric tubing; and
    circuitry in electrical communication with the heater cartridge to control a temperature of the heater block by controlling operation of the heater cartridge,
    wherein the heater block is die-cast about the tubing assembly such that the restraining component prevents the tubing from rotating within the heater block and wherein the heater block is die-cast about a first end portion of the strain relief component.

2. The apparatus of claim 1, further comprising a temperature sensor in thermal communication with the heater block to provide an indication of the temperature of the heater block, and wherein the circuitry is in electrical communication with the temperature sensor to determine therefrom the temperature of the heater block.

3. The apparatus of claim 1, wherein the tubing includes a serpentine loop, and wherein the heater block is die-cast about the serpentine loop.

4. The apparatus of claim 1, further comprising a column fitting configured to couple an end of the tube sleeve that emerges from the heater block to an inlet port of a chromatography column.

5. The apparatus of claim 1, further comprising a tube fitting configured to couple an end of the tubing extending outwardly from the heater block to an outlet port of a sample manager.

6. The apparatus of claim 1, wherein the restraining component is a hexagonally shaped sleeve.

7. The apparatus of claim 1, wherein a second end portion of the strain relief component extends outwardly from the heater block.

8. A thermal module for pre-heating liquid flowing into a liquid chromatography column, comprising:

a column compartment configured to hold a liquid chromatography column, the column compartment having an elongated trough compartment with two ends, one of the two ends having an electrical socket; and a pre-heater assembly configured to plug into the electrical socket at the one end of the trough compartment, the pre-heater assembly comprising:
  a tubing assembly comprising:
    tubing;
    a tube sleeve welded around the tubing and comprising polymeric tubing; and
    a restraining component welded around the tubing;
  a heater block made of thermally conductive material;
  a heater cartridge in thermal communication with the heater block, the heater cartridge configured to provide heat to the heater block for transfer to fluid flowing through the tubing assembly;
  a strain relief component disposed about the tubing; and
  circuitry in electrical communication with the heater cartridge to control a temperature of the heater block by controlling operation of the heater cartridge,
  wherein the heater block is die-cast about the tubing assembly such that a restraining component inhibits tubing of the tubing assembly from rotating within the heater block and wherein the heater block is die-cast about a first end portion of the strain relief component.

9. The thermal module of claim 8, further comprising a second electrical socket disposed at the other end of the trough compartment and a trough slidable within the trough compartment, the trough configured to hold a liquid chromatography column and to cover an unused one of the two electrical sockets.

10. The thermal module of claim 8, wherein one end of the trough compartment has a groove for receiving the tubing.

11. The thermal module of claim 8, wherein the pre-heater assembly further comprises a leaf-spring carrier having a pair of opposing springy prongs, and wherein the heater block assembly is disposed between the prongs.

12. The thermal module of claim 11, further comprising a receptacle configured to snap into the electrical socket of the trough compartment and to receive the leaf-spring carrier.

13. The thermal module of claim 8, further comprising a temperature sensor in thermal communication with the heater block to provide an indication of the temperature of the heater block, and wherein the circuitry is in electrical communication with the temperature sensor to determine therefrom the temperature of the heater block.

14. The thermal module of claim 8, wherein the tubing includes a serpentine loop, and wherein the heater block is die-cast about the serpentine loop.

15. The thermal module of claim 8, further comprising a column fitting configured to couple an end of the tube sleeve that emerges from the heater block to an inlet port of a chromatography column.

16. The thermal module of claim 8, further comprising a tube fitting configured to couple an end of the tubing extending outwardly from the heater block to an outlet port of a sample manager.

17. The thermal module of claim 8, wherein the restraining component is a hexagonally shaped sleeve.

18. The thermal module of claim 8, wherein a second end portion of the strain relief component extends outwardly from the heater block.

* * * * *